US012150839B2

(12) United States Patent
Stephenson

(10) Patent No.: US 12,150,839 B2
(45) Date of Patent: Nov. 26, 2024

(54) WOUND DRESSING

(71) Applicant: SYSTAGENIX WOUND MANAGEMENT, LIMITED, West Sussex (GB)

(72) Inventor: Christian Stephenson, Knutsford (GB)

(73) Assignee: Systagenix Wound Management, Limited, Bracknell (GB)

( * ) Notice: Subject to any disclaimer, the term of this patent is extended or adjusted under 35 U.S.C. 154(b) by 872 days.

(21) Appl. No.: 16/978,355

(22) PCT Filed: Mar. 8, 2019

(86) PCT No.: PCT/IB2019/051914
§ 371 (c)(1),
(2) Date: Sep. 4, 2020

(87) PCT Pub. No.: WO2019/171351
PCT Pub. Date: Sep. 12, 2019

(65) Prior Publication Data
US 2021/0000653 A1  Jan. 7, 2021

(30) Foreign Application Priority Data

Mar. 9, 2018 (GB) .................................... 1803848

(51) Int. Cl.
*A61F 13/0206* (2024.01)
*A61F 13/00* (2024.01)
(Continued)

(52) U.S. Cl.
CPC ........ *A61F 13/0209* (2013.01); *A61F 13/069* (2013.01); *A61L 26/0023* (2013.01);
(Continued)

(58) Field of Classification Search
CPC ................ A61F 13/00; A61F 13/00008; A61F 13/00021; A61F 13/00063; A61F 13/0209;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU      550575 B2    3/1986
AU      745271 B2    3/2002
(Continued)

OTHER PUBLICATIONS

Machine translation of CN-103841936-A (Year: 2014).*
(Continued)

*Primary Examiner* — Caitlin A Carreiro

(57) ABSTRACT

The present disclosure relates generally to tubular wound dressings that include a superabsorbent component that can be used to treat exuding wounds. The tubular wound dressings may include a superabsorbent component sandwiched between two tubular elastic and resilient components. Alternatively, the dressing may be concentrically arranged to include at least three components, including a superabsorbent component, and two elastic and resilient components. Also disclosed herein are kits including the tubular wound dressings of the present technology, and instructions for use.

16 Claims, 4 Drawing Sheets

(51) Int. Cl.
*A61F 13/06* (2006.01)
*A61L 26/00* (2006.01)

(52) U.S. Cl.
CPC . *A61L 26/0052* (2013.01); *A61F 2013/00093* (2013.01); *A61F 2013/00119* (2013.01); *A61F 2013/00238* (2013.01); *A61L 2300/404* (2013.01)

(58) Field of Classification Search
CPC ............ A61F 13/0266; A61F 13/00029; A61F 13/00038; A61F 13/069; A61F 13/08; A61F 13/00042; A61F 2013/00089; A61F 2013/00093; A61F 2013/00119; A61F 2013/00238; A61F 2013/00229; A61F 5/0109; A61F 17/00; A61L 26/00; A61L 26/0023; A61L 26/0052; A61L 26/0066; A61L 2300/00; A61L 2300/404; A61L 15/00; A61L 15/44
USPC .... 602/41–42, 44, 48, 58, 63; 604/304, 308; 424/443, 445, 447; 206/570
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0135171 A1* | 7/2003 | Ingram ................ A61F 13/107 604/308 |
| 2011/0208101 A1* | 8/2011 | Keller ............... A61F 13/00038 602/44 |
| 2012/0053547 A1* | 3/2012 | Schroeder ............ B32B 37/153 156/244.11 |
| 2015/0374552 A1 | 12/2015 | Lee |

FOREIGN PATENT DOCUMENTS

| | | | | |
|---|---|---|---|---|
| AU | 755496 B2 | 12/2002 | | |
| CA | 2005436 A1 | 6/1990 | | |
| CN | 103002846 A * | 3/2013 | ....... | A61F 13/15203 |
| CN | 103841936 A * | 6/2014 | ....... | A61F 13/00068 |
| DE | 26 40 413 A1 | 3/1978 | | |
| DE | 43 06 478 A1 | 9/1994 | | |
| DE | 29 504 378 U1 | 9/1995 | | |
| EP | 0100148 A1 | 2/1984 | | |
| EP | 0117632 A2 | 9/1984 | | |
| EP | 0161865 A2 | 11/1985 | | |
| EP | 0358302 A2 | 3/1990 | | |
| EP | 531096 A2 * | 3/1993 | | |
| EP | 0 642 779 A1 | 3/1995 | | |
| EP | 1018967 A1 | 7/2000 | | |
| EP | 1640023 A1 * | 3/2006 | ....... | A61F 13/00029 |
| GB | 692578 A | 6/1953 | | |

(56) References Cited

FOREIGN PATENT DOCUMENTS

| | | | | |
|---|---|---|---|---|
| GB | 2077565 | A | * 12/1981 | ........... A01K 13/007 |
| GB | 2 195 255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| JP | 4129536 | B2 | 8/2008 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/020041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | WO-2013071253 | A1 * | 5/2013 | ....... A61F 13/00063 |
| WO | WO-2015/185652 | A1 | 12/2015 | |

OTHER PUBLICATIONS

Machine translation of CN 103002846 A (Year: 2013).*

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/the British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjoörn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion in International Application No. PCT/IB2019/051914, mailed on Jun. 3, 2019.

* cited by examiner

WOUND DRESSING

CROSS-REFERENCE TO RELATED APPLICATIONS

This application is a U.S. National Phase Application under 35 U.S.C. § 371 of International Patent Application No. PCT/IB2019/051914, filed on Mar. 8, 2019, which claims the benefit of and priority to GB Patent Application No. 1803848.9, filed on Mar. 9, 2018, the contents of each of which are incorporated herein in their entirety.

BACKGROUND

A leg ulcer is a long-lasting (chronic) sore that takes more than four to six weeks to heal. They usually develop on the inside of the leg, just above the ankle.

The symptoms of a venous leg ulcer include pain, itching and swelling in the affected leg. There may also be discoloured or hardened skin around the ulcer, and the sore may produce a foul-smelling discharge.

Leg ulceration is commonly caused by venous hypertension resulting from valvular incompetence in the superficial, deep or perforating veins. Sustained venous hypertension causes swelling, restricted blood flow, and damage to the skin and other tissues. Venous disease (~80%) and arterial disease (~15%) are two of the major causes of venous ulcers.

An estimated 500,000 patients with venous ulcers are treated annually in the US. In the UK, venous ulcers are estimated to affect around 1 in 50 individuals over the age of 80. The incidence of leg ulcers is increasing as a result of the rising geriatric population and growing risk factors for atherosclerotic occlusion due to smoking, obesity and diabetes. The growing incidence of leg ulcers will subsequently drive the market for wound care products used for their treatment.

The present inventors have recognised that existing wound dressings for venous leg ulcers and similar wounds suffer from one or more of these drawbacks: (1) available absorbent wound dressings are not large enough to cover the whole of a lower leg leading to use of several absorbent dressings in a patching approach, or (2) available absorbent wound dressings are applied to the wound and then require separate application of adhesives or an outer dressing to hold the absorbent dressing in place which results in a time consuming multi-step dressing application.

SUMMARY

Due to the wide variability in size and shape of legs to be treated, standard dressings can only be partially conformable. Firstly, this variability leads to creases or wrinkles in the dressing that can lead to pressure points and sores. Secondly, such variability leads to gaps between the dressing and leg allowing wound exudate to leak leading to deterioration or maceration of the skin, thereby delaying wound healing. Leaking wound exudate can also pool leading to deterioration or maceration of additional skin. During treatment of a leg ulcer or a similar wound, a leg can initially be swollen and usually becomes less swollen with healing. Maintaining any level of conformance between the leg and the dressing requires re-dressing of the wound which requires extra time and extra patient contact. Moreover, removal and re-dressing of wounds disturbs the wound bed, which can delay healing and is painful for the patient. A dressing having features that address all of the above noted drawbacks has not previously been contemplated and would be clinically superior compared to the existing options of a patchwork of absorbent dressings held on by adhesives or a secondary layer of bandaging wrapped around a leg. The present inventors have recognised that a wound dressing that solves all of the above noted drawbacks would result in improved treatment of, and recovery from wounds such as venous leg ulcer. This is not only beneficial for the patient in that it is less painful and leads to faster wound healing, but also because of the economic benefits due to the shorter time taken to initially dress the wound, the lack of requirement for dressing changes and a reduced number of dressings being used.

The present technology therefore provides a wound dressing having the following benefits: The dressing may be tubular allowing easier dressing application to a leg. The dressing may be elastic, stretchable and resilient, which leads to improved conformance between the leg and the dressing, improved applicability to a range of leg sizes and shapes, and improved maintenance of conformance between the leg and the dressing during swelling or reduction of swelling. The dressing may be absorbent allowing wound exudate to be absorbed.

In one aspect, the present technology provides a tubular wound dressing that includes a superabsorbent component sandwiched between a first tubular elastic and resilient component and a second tubular elastic and resilient component.

In a related aspect, the present technology provides a tubular wound dressing that includes at least three concentrically arranged tubular components: (i) a first elastic and resilient component, (ii) a superabsorbent component, and (iii) a second elastic and resilient component. Additionally or alternatively, in some embodiments, each of the first elastic and resilient component, the superabsorbent component, and the second elastic and resilient component independently include a wound facing side and an environmental facing side. Additionally or alternatively, in some embodiments, the three concentrically arranged tubular components may be sealed together at the ends of the tubular wound dressing. Additionally or alternatively, in some embodiments, the tubular components (e.g., the three concentrically arranged tubular layers) may be stitched together at intervals.

In some embodiments of the tubular wound dressings of the present technology, each of the first and second elastic and resilient component includes at least one layer of an elastic and resilient material. Additionally or alternatively, in some embodiments of the tubular wound dressings of the present technology, each of the first and second elastic and resilient component comprises two layers of an elastic and resilient material. Additionally or alternatively, in some embodiments of the tubular wound dressings of the present technology, each layer of the elastic and resilient material is stretchable in at least one direction. Additionally or alternatively, in some embodiments of the tubular wound dressings of the present technology, each layer of the elastic and resilient material stretchable in two opposing directions.

Additionally or alternatively, in some embodiments, the elastic and resilient material may include a knitted material. Additionally or alternatively, in some embodiments, the elastic and resilient material may include elastane.

Additionally or alternatively, in some embodiments of the tubular wound dressings of the present technology, the superabsorbent component may include particles, fibres, or a powder of a superabsorbent polymer (SAPs), or any combination thereof. Additionally or alternatively, in some embodiments of the tubular wound dressings of the present technology, the superabsorbent component may further include an adhesive adhering the SAPs to a layer of a material.

Additionally or alternatively, in some embodiments, the SAPs may be dispersed in or on a layer of a material.

Additionally or alternatively, in some embodiments of the tubular wound dressings of the present technology, the SAPs are natural polymers, optionally selected from among celluloses and cellulose-based materials, chitosans, chitosan-based materials, hyaluronic acid, cross-linked hyaluronic acid, alginates, alginate-based materials, and any combination thereof.

Additionally or alternatively, in some embodiments of the tubular wound dressings of the present technology, the SAPs are synthetic polymers, optionally selected from among cross-linked polyacrylate sodium salts, cross-linked polymethacrylate sodium salts, and blends thereof.

Additionally or alternatively, in some embodiments, the SAPs may be at a density of from about 50 to about 450 grams per square metre (gsm) of the tubular wound dressing. Additionally or alternatively, in some embodiments, the SAPs are at a density of about 204 to about 404 gsm, of about 270 to about 335 gsm, about 274 to about 334 gsm, about 289 to about 319 gsm, or about 304 gsm, of the tubular wound dressing.

Additionally or alternatively, in some embodiments, the superabsorbent component comprises a layer of a superabsorbent material.

Additionally or alternatively, in some embodiments, the tubular wound dressing may further comprise a layer of a wicking material. Additionally or alternatively, in some embodiments, the layer of the wicking material may be located on the wound facing side of the superabsorbent component.

Additionally or alternatively, in some embodiments, the tubular wound dressing may include an antimicrobial agent. In any of the above embodiments of the tubular wound dressings of the present technology, the antimicrobial agent may be impregnated in a layer of material, for example the antimicrobial agent may be impregnated in a layer of an elastic and resilient material. Additionally or alternatively, in some embodiments, the antimicrobial agent may be silver, a silver oxysalt, iodine a quaternary ammonium salt, polyhexamethylene biguanide (PHMB), honey, or any combination thereof.

In another aspect, the present disclosure provides a method for treating a wound in a subject in need thereof, comprising dressing the wound with a tubular wound dressing of any embodiment disclosed herein. Additionally or alternatively, in some embodiments, the wound is an exuding wound or a chronic wound. Additionally or alternatively, in some embodiments, the wound is a venous leg ulcer. In some embodiments, the venous leg ulcer is caused by a venous disease or an arterial disease.

DETAILED DESCRIPTION

The wound dressing of the present technology may be tubular in shape. In some embodiments, the tubular shape is such that it can fit intimately around a limb such as a leg. The tubular shape may be shaped like a long sock without a foot portion. The tubular wound dressing may be conformable to a limb such as a leg. The tubular wound dressing may provide compression or support to a limb such as a leg.

Additionally or alternatively, in some embodiments, the wound dressing of the present technology may have at least three concentrically arranged components, including (i) a first elastic and resilient component, (ii) a superabsorbent component, and (iii) a second elastic and resilient component. In some embodiments, the superabsorbent component may be positioned between the two concentrically arranged first and second tubular elastic and resilient components.

As used herein, the "first elastic and resilient component" of a tubular wound dressing will be understood by a person of ordinary skill in the art to refer to the component which is located nearest the wound. Further, as used herein, the "second elastic and resilient component" of a tubular wound dressing will be understood by a person of ordinary skill in the art to refer to the component which is located furthest from the wound, e.g. on the exterior of the tubular wound dressing.

In any embodiment disclosed herein, each of the first elastic and resilient component, the superabsorbent component, and the second elastic and resilient component may independently include a wound facing side and an environmental facing side.

In some embodiments, the wound facing side of the second elastic and resilient component may be coupled with the environmental facing side of the superabsorbent component, wherein the wound facing side of the superabsorbent component may be coupled to the environmental facing side of the first elastic and resilient component.

Figure 1A:
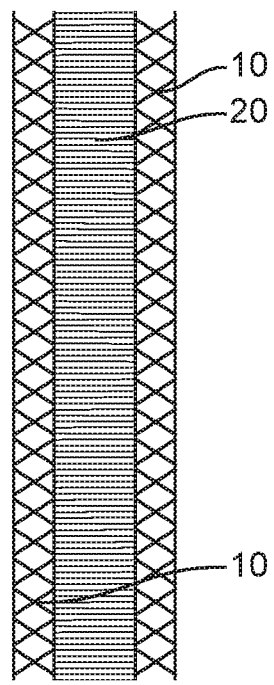
FIG. 1A shows a schematic diagram of a cross-section through a wall of a tubular wound dressing of the present technology.

FIG. 1A shows a non-limiting, schematic diagram of a cross-section, such as a longitudinal cross-section through a wall, of a tubular wound dressing of the present technology. The tubular wound dressing has a superabsorbent component [20] sandwiched in between two tubular elastic and resilient components [10]. Therefore, the tubular wound dressing has at least three concentrically arranged tubular components (e.g., tubular layers) which are a first elastic and resilient component [10], a superabsorbent component [20] and a second elastic and resilient component [10].

In any embodiment disclosed herein, each of the elastic and resilient components may be generally tubular in shape. In any embodiment disclosed herein, each elastic and resilient component can stretch in at least one direction. In this description, such a property is referred to as being elastic. After being stretched, each elastic and resilient component is capable of reverting to its original shape or an un-stretched shape or a less stretched shape, or when placed on a limb such as a leg can provide compression. In this description, such a property is referred to be as being resilient.

In any embodiment disclosed herein, each elastic and resilient component may include at least one layer of an elastic and resilient material. Additionally or alternatively, in some embodiments, each elastic and resilient component may include two layers of an elastic and resilient material.

In any embodiment disclosed herein, the elastic and resilient material allows the tubular wound dressing to conform to a limb such as a leg. Additionally or alternatively, in some embodiments, the elastic and resilient material allows the tubular wound dressing to be in intimate contact with a limb, such as a leg. Additionally or alternatively, in some embodiments, the elastic and resilient material may allow the tubular wound dressing to provide compression or support to a limb such as a leg.

In any embodiment disclosed herein, the elastic and resilient material allows the tubular wound dressing to stretch in at least one direction. Additionally or alternatively, in some embodiments, the tubular wound dressing may stretch radially, may stretch longitudinally, or may stretch both radially and longitudinally. In this description, stretching radially is stretching in one direction (e.g., along the radial axis of the tubular wound dressing) and stretching longitudinally is stretching in another separate direction (e.g., along the longitudinal axis of the tubular wound dressing). In some embodiments, the longitudinal axis of the tubular wound dressing is perpendicular to the radial axis of the tubular wound dressing. Therefore, an elastic and resilient material that may simultaneously stretch in two separate directions (e.g., can stretch both radially and longitudinally).

In some embodiments, the first and second tubular elastic and resilient components [10] may be arranged concentrically with the superabsorbent component [20]. See FIG. 1A. In any embodiment disclosed herein, each elastic and resilient component may include a single layer of an elastic and resilient material. Additionally or alternatively, in some embodiments, each elastic and resilient component may include two or more layers of an elastic and resilient material. A layer of an elastic and resilient material can be stretchable in one direction such as stretchable radially or longitudinally, or stretchable in two separate directions such as both radially and longitudinally. In any embodiment disclosed herein, each layer of an elastic and resilient material may be stretchable in one direction. Additionally or alternatively, in some embodiments, each layer of an elastic and resilient material may be stretchable in two separate directions.

In any embodiment disclosed herein, an elastic and resilient material may include a knitted material. In any embodiment disclosed herein, an elastic and resilient material may include elastic threads. Additionally or alternatively, in some embodiments, an elastic and resilient material may include elastane (for example Spandex™ or Lycra™ (DuPont, Wilmington, DE) which may be a polyether-polyurea copolymer), rubber or latex or latex-free elastic yarns (which may be useful if there is a risk of a latex allergy in a patient).

Additionally or alternatively, in some embodiments, an elastic and resilient material may include, but is not limited to, cotton and elastic yarns, or cotton, polyester and elastic yarns (optionally latex-free elastic yarns). In any embodiment disclosed herein, the ratio of cotton, and the elastic yarns (and optionally polyester) may be varied to provide differing grades of elasticity and resilience. Additionally or alternatively, in some embodiments, the elastic and resilient material may include cotton (for example 70 to 90%) and other elastic yarns, such as rubber (for example 10 to 30%). Additionally or alternatively, in some embodiments, the cotton included in the elastic and resilient material is in an amount of about 70%, 72%, 74%, 76%, 78%, 80%, 82%, 84%, 86%, 88%, 90%, or any range including and/or in between any two of the preceding values. Additionally or alternatively, in some embodiments, the elastic yarns (e.g., rubber) included in the elastic and resilient material is in an amount of 10%, 12%, 14%, 16%, 18%, 20%, 22%, 24%, 26%, 28%, 30%, or any range including and/or in between any two of the preceding values.

In any embodiment disclosed herein, an elastic and resilient material may be an elasticated tubular bandage, for example a heavy cotton weave material with elastic threads laid into the material to form a continuous spiral. One commercially available example is Tubigrip™ (Mölnlycke Healthcare, Norcross, GA). Another example is Elastogrip™ (BSN Medical, Inc., Charlotte, NC), which is a polyester and spandex tubular elastic compression bandage.

In any embodiment disclosed herein, an elastic and resilient material may be a tubular net bandage. Additionally or alternatively, in some embodiments, the tubular net bandage may include cotton/polyamide/elastic thread. A tubular net dressing structure allows for stretch in more than one direction. A commercially available source of a net tubular bandage is Medelast™, (Ningbo Medelast Co, Ltd., Ningbo, China).

In any embodiment disclosed herein, an elastic and resilient material can be a cotton crepe tubular bandage.

Additionally or alternatively, in some embodiments, the tubular wound dressing of the present technology may include a plurality of layers of the elastic and resilient material. Additionally or alternatively, in some embodiments, each layer of an elastic and resilient material may be independently selected from available elastic and resilient materials.

In any embodiment disclosed herein, the superabsorbent component may absorb fluid such as wound exudate. Therefore, the tubular wound dressing of the present technology may be used in the treatment or management of acute or chronic wounds, for example leg ulcers which can be venous leg ulcers. A treatment using a tubular wound dressing of the present technology supports exudate migration and/or absorption and retention. The treatment can result in the formation or healing of tissue in a wound to which a tubular wound dressing of the present technology is applied.

In any embodiment disclosed herein, the superabsorbent component may include a superabsorbent polymer.

In any embodiment disclosed herein, the superabsorbent polymer may be in the form of fibres, particles, or a powder, or any combination thereof, of a superabsorbent polymer (SAPs). The particles or fibres or powder of SAPs may be dispersed on or within a layer of material. In any embodiment disclosed herein, the superabsorbent polymer may further include an adhesive adhering the SAPs to a layer of a material. Additionally or alternatively, in some embodiments, the SAPs may be adhered to one side of the layer of material or to two sides of the layer of material. Additionally or alternatively, in some embodiments, the SAPs may be adhered to the layer of material by powder adhesive or by a wet adhesive applied to the layer of material. Additionally or alternatively, in some embodiments, the SAPs may be adhered to a layer of a woven or a non-woven material. Additionally or alternatively, in some embodiments, the SAPs may be adhered to a layer of an elastic and resilient material disclosed herein.

In any embodiment disclosed herein, the superabsorbent component may include more than one superabsorbent polymer. Additionally or alternatively, in some embodiments, the superabsorbent component may include two or three or more types of superabsorbent polymer.

In any embodiment disclosed herein, the superabsorbent polymer may be a synthetic or a natural polymer. Suitable natural superabsorbent polymers may include, but are not limited to, natural biomaterials, such as celluloses, chitosans, hyaluronic acids and alginates; materials made from naturally occurring biomaterials, for example cellulose-based materials, such as carboxymethylcellulose materials, chitosan-based materials, such as carboxymethylchitosan materials, and alginate-based materials; and hydrogel precursors, for example those based on carboxymethylcellulose materials, carboxymethylchitosan materials, and alginate materials, poly(vinyl alcohol) and poly(ethylene oxide). Suitable synthetic superabsorbent polymers may include, but are not limited to, synthetic polymers, such as pharmaceutically acceptable salts of poly(acrylic and/or methacrylic) acids, cross-linked polyacrylate and polymethacrylate salts, for example alkali metal salts thereof, and copolymers and blends thereof; cross-linked polyacrylate sodium salts, and cross-linked polymethacrylate sodium salts, and blends thereof; in particular cross-linked sodium polyacrylates.

In any embodiment disclosed herein, the absorbency of the superabsorbent polymer is of the order of 15 to 60 g/g of 0.9% saline, for example about 20 to 30 g/g of 0.9% saline. As used herein, the term "g/g" refers to the mass of saline (g) absorbed per mass of the superabsorbent polymer (g). Additionally or alternatively, in some embodiments, the absorbency of the superabsorbent polymer is of the order of 15 g/g of 0.9% saline, 20 g/g of 0.9% saline, 25 g/g of 0.9% saline, 30 g/g of 0.9% saline, 35 g/g of 0.9% saline, 40 g/g of 0.9% saline, 45 g/g of 0.9% saline, 50 g/g of 0.9% saline, 55 g/g of 0.9% saline, 60 g/g of 0.9% saline, or any range including and/or in between any two of the preceding values. This enables large quantities of fluid such as wound exudate to be absorbed into the superabsorbent polymer.

In any embodiment disclosed herein, the SAPs may be at a density of from about 50 to about 450 grams per square metre (gsm) of the tubular wound dressing. Additionally or alternatively, in some embodiments, the SAPs may be at a density of from about 50 gsm, about 55 gsm, about 60 gsm, about 65 gsm, about 70 gsm, about 75 gsm, about 80 gsm, about 85 gsm, about 90 gsm, about 95 gsm, about 100 gsm, about 110 gsm, about 120 gsm, about 130 gsm, about 140 gsm, about 150 gsm, about 160 gsm, about 170 gsm, about 180 gsm, about 190 gsm, about 200 gsm, about 220 gsm, about 240 gsm, about 260 gsm, about 280 gsm, about 300 gsm, about 320 gsm, about 340 gsm, about 360 gsm, about 380 gsm, about 400 gsm, about 420 gsm, about 440 gsm, about 450 gsm, or any range including and/or in between any two of the preceding values. The density of SAPs may vary with the type of superabsorbent polymer used and the person skilled in the art can select a suitable density. The SAPs may be at a density of more than 50 gsm, more than 100 gsm, more than 150 gsm, more than 200 gsm, or more than 250 gsm of the tubular wound dressing. The SAPs may be at a density of less than 450 gsm, less than 400 gsm, or less than 350 gsm of the tubular wound dressing. The SAPs may be at a density of about 200 gsm to about 400 gsm, of about 250 gsm to about 350 gsm, or about 300 gsm of the tubular wound dressing. The SAPs may be at a density of about 204 gsm to about 404 gsm, of about 270 gsm to about 335 gsm, about 274 gsm to about 334 gsm, about 289 gsm to about 319 gsm, or about 304 gsm of the tubular wound dressing.

The term "non-woven" herein in relation to fabrics means that the majority of fibres in the fabric are neither woven nor knit together to form a sheet or web. They are typically manufactured by putting small fibres, typically microfibers as defined micrometres, together to form a sheet or web, and then binding them together. They may be bound mechanically (as in the case of felt, by interlocking them with serrated needles such that the inter-fibre friction results in a stronger fabric), with an adhesive, or thermal bonding, for example by spin-bonding (with solution or melt spinning, or melt-blowing). Spin-bonding is an exemplary method of manufacture because it readily allows scale-up to industrial levels of production, particularly in terms of appropriately sized absorbent components for use in medical applications.

In any embodiment disclosed herein, the superabsorbent component may include a layer of a superabsorbent material.

In any embodiment disclosed herein, the superabsorbent material may be a non-woven superabsorbent material. Suitable superabsorbent materials include the range of Super Absorbent Fibres (SAF™) from Technical Absorbents Ltd (Grimsby, United, Kingdom).

A superabsorbent material may absorb a fluid, such as wound exudate, extremely quickly. For example the SAF™ fibre range can absorb up to 200 times its own weight in demineralised water and about 60 times its own weight in saline.

In any embodiment disclosed herein, the superabsorbent component may include a layer of a stretchable material in or on which SAPs may be dispersed or adhered. Additionally or alternatively, in some embodiments, the layer of stretchable material may be a non-woven material, the fibres of which can stretch (and would not break).

In any embodiment disclosed herein, the tubular wound dressing may further include a layer of a wicking material. Additionally or alternatively, in some embodiments, the layer of a wicking material may be located on the wound facing side of the superabsorbent component. Additionally or alternatively, in some embodiments, the wicking material may be hydrophilic. Additionally or alternatively, in some embodiments, the layer of a wicking material may assist in the spread of fluid, such as wound exudate, away from the exuding location across the tubular wound dressing. Additionally or alternatively, in some embodiments, the layer of a wicking material may help distribute fluid, such as wound exudate, away from the wound or away from the exuding location. In any embodiment disclosed herein, the wicking material may be a synthetic material blended with another material. Additionally or alternatively, in some embodiments, the wicking material can be a 50 gsm polyester viscose mix (35% Polyester, 65% viscose).

The term "hydrophilic" herein in relation to a material refers to any substantially water-insoluble material which when water or an aqueous medium is in contact with it, is wetted by water or the medium.

In any embodiment disclosed herein, hydrophilic materials include, but are not limited to, polymeric materials, for example natural materials, such as celluloses, chitosans, hyaluronic acids and alginates; polymeric materials made from naturally occurring biomaterials, for example alginate-based materials, cellulose-based materials, such as carboxymethylcellulose materials, chitosan-based materials, such as carboxymethylchitosan materials, and synthetic polymeric materials, such as certain polyurethanes, copoly(etheresters), poly(alkylene oxides), polyamides, polycarbonates and polyorthoesters, and any combination thereof.

In any embodiment disclosed herein, the tubular wound dressing may include a layer of a fluid-permeable, hydrophobic material. Additionally or alternatively, in some embodiments, the layer of the fluid-permeable, hydrophobic material may be located on the wound facing side of the tubular wound dressing (e.g., wound facing side of the first elastic and resilient component (FIG. 1A; [10]). Additionally or alternatively, in some embodiments, the layer of the fluid-permeable, hydrophobic material can, in use, contact the wound. Additionally or alternatively, in some embodiments, the layer can allow fluid such as wound exudate to pass through, for example, towards the superabsorbent component. Additionally or alternatively, in some embodiments, the layer of a fluid-permeable, hydrophobic material can be polyester.

The term "hydrophobic" herein in relation to a material refers to any substantially water-insoluble material which when water or an aqueous medium is in contact with it, is not wetted by water or the medium. Examples of hydrophobic materials useful in the tubular wound dressings disclosed herein include, but are not limited to, synthetic materials, such as polyalkylenes, for example low- and high-density polyethylene, polypropylene and polybutylene; poly(vinyl chloride), polystyrene, polyamides, poly(tetrafluoroethylene), thermoplastic polyurethanes, and any combination thereof.

In any embodiment disclosed herein, the tubular wound dressing may include a layer to aid wound detachment. Additionally or alternatively, in some embodiments, the wound detachment layer may have a shiny surface. Additionally or alternatively, in some embodiments, the wound detachment layer may prevent a healing wound from adhering to a dressing. Additionally or alternatively, in some embodiments, the wound detachment layer may prevent disturbance of the wound bed when a wound dressing is removed. Additionally or alternatively, in some embodiments, the wound detachment layer is generally on the wound facing surface of the tubular wound dressing (e.g., wound facing side of the first elastic and resilient component (FIG. 1A, [10]).

In any embodiment disclosed herein, a first tubular elastic and resilient component and a second tubular elastic and resilient component may be fixed together, sandwiching a superabsorbent between the two components, to form a single tubular wound dressing. In this way the tubular wound dressing may be easily and rapidly applied to a limb such as a leg. Additionally or alternatively, in some embodiments, the first tubular elastic and resilient component and the second tubular elastic and resilient component may be sealed together at the ends of the tubular components to form the tubular wound dressing. Additionally or alternatively, in some embodiments, the first tubular elastic and resilient component and the second tubular elastic and resilient component may be stitched together at intervals along the longitudinal dimension. Additionally or alternatively, in some embodiments, the first tubular elastic and resilient component and the second tubular elastic and resilient component may be fixed together to form the tubular wound dressing by both sealing at the ends of the tubular components and stitching together at intervals along its length.

In any embodiment disclosed herein, at least the first and second tubular elastic and resilient components may be of the same length. Additionally or alternatively, in some embodiments, the first and second tubular elastic and resilient components and the superabsorbent component may be of the same length. Additionally or alternatively, in some embodiments, the first and second tubular elastic and resilient components and the superabsorbent component may be of equal length. Additionally or alternatively, in some embodiments, one or more components or one or more layers (e.g., superabsorbent component) that are sandwiched between the tubular elastic and resilient components may be of shorter length than the tubular elastic and resilient components.

In any embodiment disclosed herein, the tubular wound dressing of the present technology may further comprise an antimicrobial agent. Additionally or alternatively, in some embodiments, the antimicrobial agent includes an agent with antibacterial properties and/or antimycotic properties and/or antiviral properties. Examples of microbes that can be found at wounds and against which antimicrobial agents can be used include, but are not limited to, bacteria such as Methicillin-resistant *Staphylococcus aureus* (MRSA), *Clostridium difficile, Salmonella typhimurium, Leigonella, Listeria monocytogenes* and *Escherichia coli*; and fungi such as *Aspergillus niger* and *Candida albicans*.

In any embodiment disclosed herein, antimicrobial agents which may be included in a tubular wound dressing of the present technology include silver, a silver oxysalt, iodine, a quaternary ammonium salt, a derivitized quaternary ammonium salt, polyhexamethylene biguanide (PHMB), honey, or any combination thereof.

Reference to a "derivatized quaternary ammonium salt" herein is to a substance which is a quaternary ammonium salt which is derivatized by being N-substituted by a tris (hydrocarbyl or hydrocarbyloxy)-silylhydrocarbyl group.

In any embodiment disclosed herein, the antimicrobial agent may be impregnated into a layer of material of the tubular wound dressing. Additionally or alternatively, in some embodiments, the antimicrobial agent may be impregnated into a layer of elastic and resilient material. Additionally or alternatively, in some embodiments, the antimicrobial agent may be impregnated into the wound facing side of the first elastic and resilient material. Additionally or alternatively, in some embodiments, the antimicrobial agent may be impregnated into another stretchable layer of material of the tubular wound dressing.

Figure 2A:
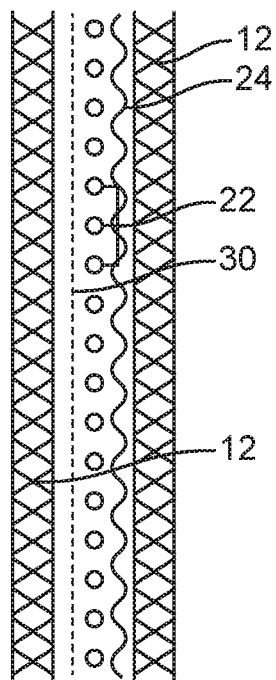
FIGS. 2A and 2B illustrate two, non-limiting, embodiments of a wound dressing of the present technology comprising more than three concentrically arranged components.
Figure 2B:
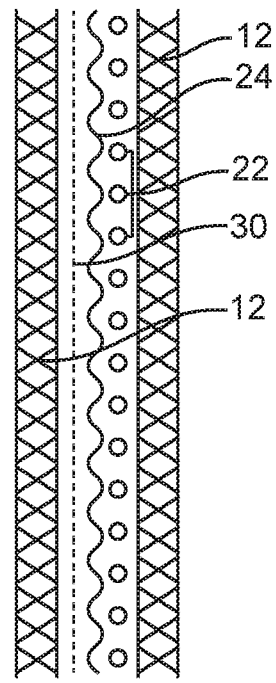

It is envisaged that a layer of a wicking material (FIG. 2B, (30)) or a layer of material including an antimicrobial agent, if present, may be positioned between each of the first and second tubular elastic and resilient components.

Additionally or alternatively, in some embodiments, the tubular wound dressing may have an alternative layer outside of the first elastic and resilient component. Additionally or alternatively, in some embodiments, the alternative layer includes a wound facing side and an environmental facing side. Additionally or alternatively, in some embodiments, the environmental facing side of the alternative layer may be coupled with the wound facing side of the first elastic and resilient component. Thus, the wound facing side of the alternative layer may be configured to be in contact with a wound when in use. For example, the tubular wound dressing may have a layer of a fluid-permeable, hydrophobic material, or a layer of a wicking material or a layer to aid wound detachment outside an elastic and resilient component. Therefore a tubular wound dressing may have a layer of a fluid-permeable, hydrophobic material, or a layer of a wicking material or a layer to aid wound detachment as a wound facing layer which is use is wound contacting.

The present technology also embraces a method of treating a wound in a subject in need thereof, where the method includes dressing the wound with the tubular wound dressing of any embodiment disclosed herein. Additionally or alternatively, in some embodiments, the wound is an exuding wound or a chronic wound. Additionally or alternatively, in some embodiments, the wound may include an ulcer (e.g., a leg ulcer). Additionally or alternatively, in some embodiments, the wound may include a venous leg ulcer. The method comprises applying the tubular wound dressing of the present technology to the afflicted limb, such as a leg.

In a further related aspect, the present disclosure provides kits that include a tubular wound dressing of any embodiment described herein and instructions for use. The kits of the present technology may also include instructions for methods for treating a wound in a subject or patient in need thereof. The kit may optionally comprise components such as antiseptic wipes, ointment, adhesive tape, tweezers, scissors, etc.

EXAMPLES

Example 1

Figure 1B:
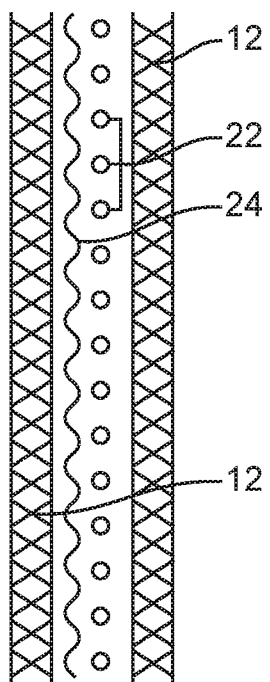
FIGS. 1B and 1C illustrate two, non-limiting, embodiments of a wound dressing of the present technology that comprises three concentrically arranged components.
Figure 1C:
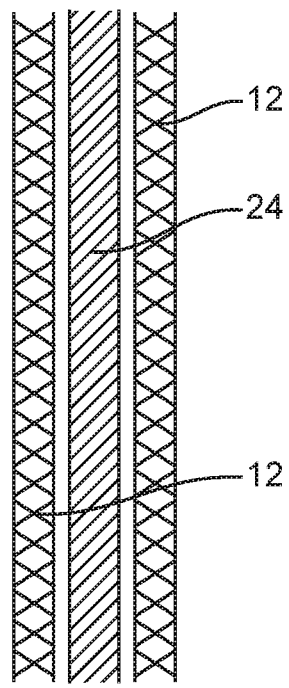

FIGS. 1B and 1C illustrate two, non-limiting, embodiments of the present technology which have three concentrically arranged tubular components: an elastic and resilient component, a superabsorbent component, and another elastic and resilient component.

FIG. 1B illustrates a, non-limiting, embodiment of the present technology as a partially exploded cross-section through a tubular wound dressing. The tubular wound dressing has two concentrically arranged layers of an elastic and resilient material [12]. The tubular wound dressing has SAPs [22] sandwiched between the two concentrically arranged tubular layers of an elastic and resilient material [12]. The SAPs [22] are adhered to a layer of elastic and resilient material by an adhesive [24].

FIG. 1C illustrates another, non-limiting, embodiment of the present technology as a partially exploded cross-section through a tubular wound dressing. The tubular wound dressing has two concentrically arranged layers of an elastic and resilient material [12]. The tubular wound dressing has a layer of a superabsorbent material [24] sandwiched between the two concentrically arranged tubular layers of an elastic and resilient material [12].

Example 2

FIGS. 2A and 2B illustrate two, non-limiting, embodiments of the present technology which have more than three concentrically arranged tubular components. In comparison with the embodiments of Example 1, the embodiments in FIGS. 2A and 2B additionally have a layer of a wicking material.

FIG. 2A illustrates a, non-limiting, embodiment of the present technology as a partially exploded cross-section through a tubular wound dressing. The tubular wound dressing has two concentrically arranged layers of an elastic and resilient material [12]. The tubular wound dressing has SAPs [22] sandwiched between the two concentrically arranged tubular layers of an elastic and resilient material [12]. The SAPs [22] are adhered to a layer of elastic and resilient material by an adhesive [24]. The tubular wound dressing also has a layer of a wicking material [30] sandwiched between the two concentrically arranged tubular layers of an elastic and resilient material [12]. FIG. 2B shows an alternative, non-limiting, embodiment in which the SAPs [22] are adhered to the layer of a wicking material [30]. In use, it is envisioned that the layer of a wicking material [30] will be located on the wound facing side of the SAPs [22].

Example 3

Figure 3:
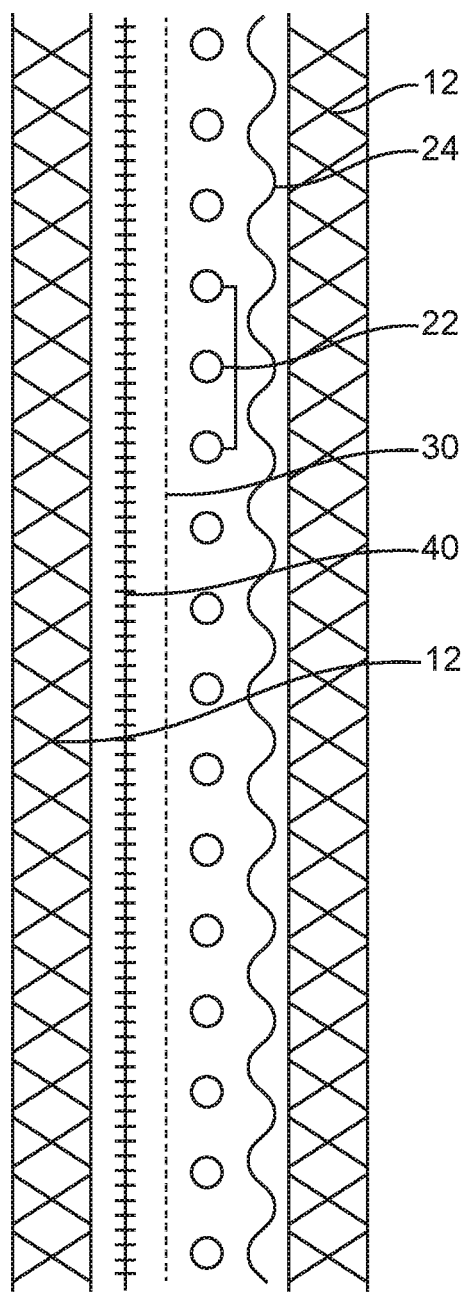
FIG. 3 illustrates a, non-limiting, embodiment of a wound dressing of the present technology comprising more than three concentrically arranged components.

FIG. 3 illustrates a, non-limiting, embodiment of the present technology which has more than three concentrically arranged tubular components. In comparison with the embodiments of Example 2, the embodiment in FIG. 3 additionally has a layer comprising an antimicrobial agent.

FIG. 3 illustrates a, non-limiting, embodiment of the present technology as a partially exploded cross-section through a tubular wound dressing. The tubular wound dressing has two concentrically arranged layers of an elastic and resilient material [12]. The tubular wound dressing has SAPs [22] sandwiched between the two concentrically arranged tubular layers of an elastic and resilient material [12]. The SAPs [22] are adhered to a layer of elastic and resilient material by an adhesive [24]. The tubular wound dressing also has a layer of a wicking material [30] and an antimicrobial agent [40] sandwiched between the two concentrically arranged tubular layers of an elastic and resilient material [12]. The antimicrobial agent [40] is impregnated onto a layer of elastic and resilient material that, in use, is on the wound facing side of the tubular dressing.

It will be understood the arrangement of the layers sandwiched between the two tubular elastic and resilient components may be different from that illustrated in the attached figures.

Example 4

Figure 4A:
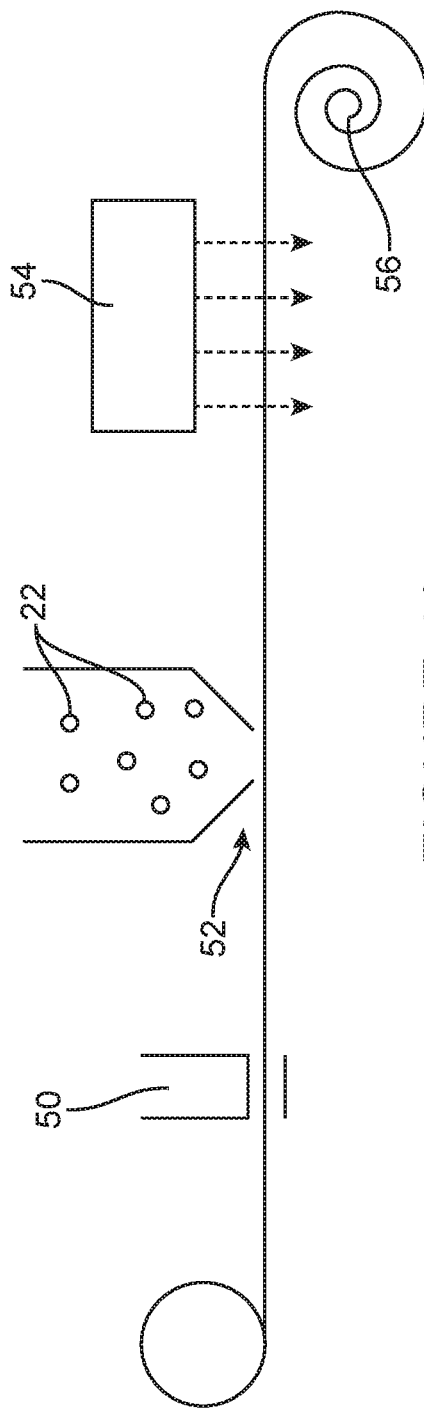
FIGS. 4A and 4B show part of the manufacturing process for making a tubular wound dressing of the present technology.
Figure 4B:
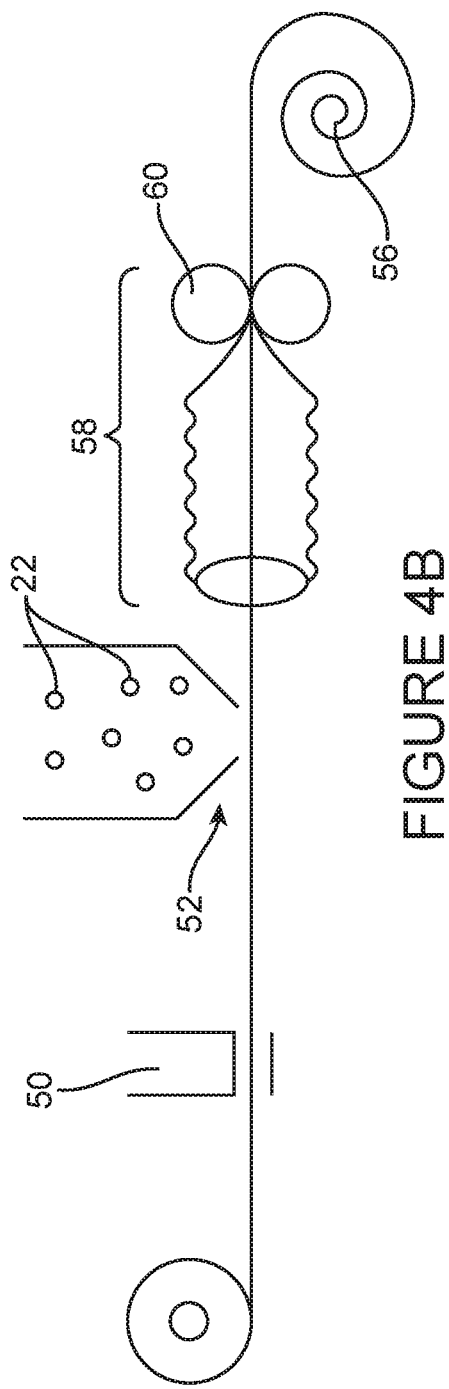

FIG. 4 illustrates part of the manufacturing process of a tubular wound dressing according to the present technology. The process was carried out on an indent machine. FIG. 4A shows that via a nip roller [50] a water based adhesive was coated onto one side of a tubular material. In some embodiments, the tubular material can be an elastic and resilient material. Additionally or alternatively, in some embodiments, the tubular material can be a non-woven material. The material then passed under a scatter head [52] which dispensed SAPs [22] onto the glue coated material. The scatter head [52] is important to ensure even coating of the SAPs [22] onto the non-woven material. The scatter head [52] was fed from a large reservoir above it into which SAPs were poured. The coated non-woven material was passed through a heater [54] to set the adhesive and collected on a spool roller [56]. This created a superabsorbent component. The material of the tubular absorbent component was then reversed as shown in FIG. 4B and the other side was put back through the same process. However, before being collected on the spool roller [56], the tubular elastic and resilient material to which SAPs [22] have been adhered was passed through a second tubular layer of an elastic and resilient material, similar to that of a sausage filling machine [58]. The tubular wound dressing material was then passed through another nip roller [60] and collected. Once the composite tubular wound dressing was complete; the product was cut to size and ends sealed with a heat sealer.

The invention claimed is:

1. A tubular wound dressing comprising:
   a first elastic and resilient component, the first elastic and resilient component being tubular and having a wound facing side and an environmental facing side, the first elastic and resilient component having an antimicrobial agent dispersed into pores of the first elastic and resilient component;
   a second elastic and resilient component the second elastic and resilient component being tubular and having a wound facing side and an environmental facing side, the wound facing side of the second elastic and resilient component facing the environmental facing side of the first elastic and resilient component;
   a superabsorbent component sandwiched between the first elastic and resilient component and the second elastic and resilient component, the superabsorbent component having a wound facing side and an environmental facing side;

a layer of fluid-permeable hydrophobic material having a wound facing side and an environmental facing side, the environmental facing side of the layer of fluid-permeable hydrophobic material facing the wound facing side of the first elastic and resilient component;

a layer of wicking material having a wound facing side and an environmental facing side, the wound facing side of the layer of wicking material facing the environmental facing side of the first elastic and resilient component, the superabsorbent component being adhered to the environmental facing side of the layer of wicking material;

each of the first elastic and resilient component, the second elastic and resilient component, the superabsorbent component, and the layer of fluid-permeable material being concentrically arranged.

2. The tubular wound dressing of claim 1, wherein the superabsorbent component comprises particles, fibres, or a powder, or any combination thereof, of a superabsorbent polymer (SAPs), wherein the superabsorbent component further comprises an adhesive adhering the SAPs to a layer of a material.

3. The tubular wound dressing of claim 2, wherein the SAPs are dispersed in or on a layer of a material.

4. The tubular wound dressing of claim 2, wherein the SAPs are natural polymers, selected from celluloses and cellulose-based materials, chitosans and chitosan-based materials, hyaluronic acid, cross-linked hyaluronic acid, alginates and alginate-based materials.

5. The tubular wound dressing of claim 2, wherein the SAPs are synthetic polymers, selected from cross-linked polyacrylate sodium salts, and cross-linked polymethacrylate sodium salts, and blends thereof.

6. The tubular wound dressing of claim 2, wherein the SAPs are at a density of from about 50 to about 450 grams per square metre (gsm), about 204 to about 404 gsm, about 270 to about 335 gsm, about 274 to about 334 gsm, about 289 to about 319 gsm, or about 304 gsm, of the tubular wound dressing.

7. The tubular wound dressing of claim 1, wherein each of the first and second elastic and resilient components independently comprise at least one layer of an elastic and resilient material or two layers of an elastic and resilient material.

8. The tubular wound dressing of claim 7, wherein each layer of an elastic and resilient material is stretchable in at least one direction or in two opposing directions.

9. The tubular wound dressing according to claim 7, wherein the elastic and resilient material comprises a knitted material or elastane.

10. The tubular wound dressing of claim 1, wherein the superabsorbent component comprises a layer of a superabsorbent material.

11. The tubular wound dressing of claim 1, wherein the antimicrobial agent is silver, a silver oxysalt, iodine, a quaternary ammonium salt, polyhexamethylene biguanide (PHMB), honey, or any combination thereof.

12. The tubular wound dressing of claim 1, wherein the first tubular elastic and resilient component and the second tubular elastic and resilient component may be sealed together at the ends of the components to form the tubular wound dressing.

13. The tubular wound dressing of claim 1, wherein the first tubular elastic and resilient component and the second tubular elastic and resilient component may be stitched together at intervals along a longitudinal direction.

14. A method of treating a wound in a subject in need thereof, comprising dressing the wound with the tubular wound dressing of claim 1.

15. The method of claim 14, wherein the wound is an exuding wound or a venous leg ulcer.

16. A kit comprising the tubular wound dressing of claim 1, and instructions for use.

* * * * *